(12) United States Patent
Abraham et al.

(10) Patent No.: US 8,475,731 B2
(45) Date of Patent: Jul. 2, 2013

(54) LATERAL FLOW ASSAY READER WITH TRANSPARENT BARRIER IN INSERT

(75) Inventors: Rami H. Abraham, Millis, MA (US); Stanley E. Charm, Boston, MA (US)

(73) Assignee: Charm Sciences, Inc., Lawrence, MA (US)

( * ) Notice: Subject to any disclaimer, the term of this patent is extended or adjusted under 35 U.S.C. 154(b) by 433 days.

(21) Appl. No.: 12/678,388

(22) PCT Filed: Sep. 22, 2008

(86) PCT No.: PCT/US2008/010952
§ 371 (c)(1),
(2), (4) Date: Aug. 18, 2010

(87) PCT Pub. No.: WO2009/038798
PCT Pub. Date: Mar. 26, 2009

(65) Prior Publication Data
US 2010/0311181 A1    Dec. 9, 2010

Related U.S. Application Data (60) Provisional application No. 60/974,183, filed on Sep. 21, 2007.

(51) Int. Cl.
*G01N 21/75* (2006.01)
(52) U.S. Cl.
USPC .................. 422/402; 422/400; 422/401
(58) Field of Classification Search
None
See application file for complete search history.

(56) References Cited

U.S. PATENT DOCUMENTS

| | | | |
|---|---|---|---|
| 6,998,273 B1 | 2/2006 | Fleming et al. | |
| 2002/0155028 A1 | 10/2002 | Wong | |
| 2004/0021089 A1 | 2/2004 | Cimino et al. | |
| 2004/0247898 A1 | 12/2004 | Ogawa | |
| 2005/0036148 A1* | 2/2005 | Phelan | 356/446 |
| 2005/0074899 A1 | 4/2005 | Polito et al. | |
| 2005/0264817 A1 | 12/2005 | Havard et al. | |
| 2006/0014213 A1 | 1/2006 | Tang et al. | |
| 2006/0106373 A1 | 5/2006 | Cahir et al. | |
| 2006/0166374 A1 | 7/2006 | Hubscher | |
| 2007/0177147 A1 | 8/2007 | Parce | |

FOREIGN PATENT DOCUMENTS

| | | | |
|---|---|---|---|
| EP | 0837320 A2 | 8/1997 | |
| EP | 1033569 A1 | 2/2000 | |

* cited by examiner

*Primary Examiner* — Yelena G Gakh
(74) *Attorney, Agent, or Firm* — MacCord Mason PLLC (57) ABSTRACT

An assay reader system incorporating a conventional assay reader, for example a lateral flow reader, and an insert aligned with the reader's sensor to detect an assay result. The insert may include a housing which defines a cavity to receive a removable barrier, wherein the removable barrier can be aligned between the sensor and the test strip. The barrier may include an optical window, and may be cleanable and/or disposable to maintain the accuracy of the reader. Test strips are introduced into the reader through a receiving port within the insert's housing. An air inlet on the insert further maintains the reader's accuracy by allowing air to be tunneled over the housing to remove excess dust, debris, or the like.

21 Claims, 12 Drawing Sheets

LATERAL FLOW ASSAY READER WITH TRANSPARENT BARRIER IN INSERT

REFERENCE TO PRIOR APPLICATION

This application is based on and claims priority from U.S. Provisional Patent Application No. 60/974,183, filed on Sep. 21, 2007, the teachings of which are incorporated herein by this reference.

FIELD

This disclosure relates generally to an apparatus and method for assay reader analysis, and, more particularly, to an insert for an assay reader system.

BACKGROUND

Reagent strips and films are an important analytical tool in the fields of clinical chemistry, analytical medicine and food sanitation diagnostics. In some cases, colorimetric detection schemes are used to measure the concentration of analytes on such strips and films. One type of test strip assay is a lateral flow assay. Generally, lateral flow assays are membrane-based test devices in which a sample that is suspected of containing the analyte of interest is placed at or near one end of the membrane strip. The sample is carried to the opposite end of the membrane strip by a mobile, i.e liquid phase that traverses the membrane strip by capillary action. While traversing the membrane strip, the analyte in the test sample, if any, encounters one or more reagents. The reagents can include binders for the analyte. Binders can be mobile and, therefore, flow with the sample or be immobilized on the test strip as a capture agent. Depending on the assay configuration, either the analyte binder, the analyte itself, or some other reagent in the assay system, will be captured by the immobilized capture agent and, thereby, produce a detectable signal. The signal can be generated by a label provided within the assay. The detectable signal can be measured by a reader, such as by an optical reader.

Optical analysis reader systems can include a light source, a sample, and an optical detector aligned such that the light from the light source illuminates onto the test strip and is then refracted or refracted onto the detector. The light source can include an incandescent bulb, a fluorescent tube, a light emitting diode, or the like. An example of such an optical reader is described in U.S. Pat. No. 6,124,585 (Apparatus for Measuring the Reflectance of Strips Having Non-uniform Color), issued Sep. 26, 2000, and incorporated herein by reference.

The presence and, in some cases, the concentration, of an analyte on a reagent strip sample may be determined by measuring the optical reflectance or refractance from an area of color development on the strip. Percent reflectance can be used to determine the result. The light source can be positioned to generate a light pattern on the target surface which is reflected onto an optical detector. The light source can be positioned in variety of ways and in a variety of configurations relative to the optics.

Regardless of the configuration used to illuminate the test strip onto the system optics, contamination of the optics can disrupt system measurements. Test strips are used for a variety of detection applications in a variety of matrices such as blood, urine and food. An example of such a test strip is described in U.S. Pat. No. 7,097,983 (Method for Detecting the Presence of an Analyte in a Sample), issued Aug. 29, 2006, incorporated herein by reference.

When test strips are used, for example, to detect drug residues in foods, such as milk, it is possible that food residue will remain on either or both the test strip or the test strip package when inserted into the reader. If the food residue or the like disrupts the analysis, such as by disrupting the light reflectance/refraction pattern, incorrect test results can occur. Similarly, dust or other contaminants can contaminate the optics and disrupt test results. When test results are disrupted by contaminants, readers must be either recalibrated or cleaned. The recalibration and/or cleaning processes can be time consuming and expensive.

SUMMARY

The present invention relates to an apparatus and method for operating and maintaining an assay reader free from the disadvantages of the prior art. Various aspects include a reader, such as for example a lateral flow assay reader, insert and method for maintaining the reader insert for consistent test results. In some embodiments, the reader can be configured to detect an assay result from a lateral flow test strip, for example, from the binding of a detectable analyte within one or more areas on the test strip. In one embodiment of the disclosure, the insert can include a housing having an exterior and an interior. A cavity defined by the housing can have a depth to allow a barrier to align between the test strip and the sensor on the reader. A receiving port can be positioned within the housing for admitting a test strip from the exterior of the housing to the interior of the reader housing, whereby the test strip can be exposed to the reader's sensor.

Such removable barriers can be used with a variety of optical systems. In one embodiment of the disclosure, the optical reader can include a light source, positioned to illuminate the test strip and a sensor, such as an optical sensor, positioned relative to the test strip so that changes on the test strip can be detected. In yet a further embodiment, the removable barrier can be made of optically clear material so that light can shine through with minimal refraction. In embodiments where the refraction caused by the barrier cannot be eliminated, the refraction can be offset by calibration of the reader. In some aspects, the removable barrier is cleanable and/or disposable and can be engaged and removed from the cavity by a handle or the like. An example of material useful in making such an optically clear window includes material with a low refractive index such as clear polyvinyl chloride plastic, or any other clear plastic, fused silica glass, fused quartz and acrylics.

When optical sensors are utilized in the reader, various optical sensors may be useful including a single photodiode, multiple photodiodes, a linear photodiode array, a charged couple device (CCD) and a complementary metal oxide semiconductor (CMOS) image sensor. The optical sensor and the light source can be positioned in a variety of locations including above the test strip or below the test strip. When the optical sensor is above the test strip, the removable barrier, or the optical window, will also be positioned in alignment above the test strip. To further improve accuracy of the reader, embodiments of the disclosure can also include an air inlet configured to allow air to be blown into and funneled through the device. Such blown air can be used to further clean the inside of the device.

Only certain embodiments of this disclosure have been suggested in the above summary and will be shown or described in the following description and figures. The closet prior art known to the applicant does not disclose embodiments of this disclosure, nor are the embodiments of the disclosure obvious, alone or in combination thereof. These

DETAILED DESCRIPTION

The following description includes like reference characters that correspond to like elements throughout the several figures. The terms 'left,' 'right,' 'forward,' 'rearward,' and the like are words of convenience to describe various embodiments and should not be construed as limitations to the scope of the invention. Referring now to the drawings in general and FIG. 1 in particular, the views are for the benefit of describing a preferred embodiment of the disclosure and are not intended to limit the invention thereto. It is to be understood that modifications to the dimensions, figures, and descriptions of the designs are within the spirit of the invention.

A variety of readers can be usefully employed by the reader insert including, for example, fluorometers, luminometers, bar code readers, radiation detectors (such as scintillation counters), UV detectors, infrared detectors, cameras, electrochemical detectors or optical readers, such as spectrophotometers. Such readers are used to determine results on a test strip.

In one embodiment an optical system is used to measure the reflectance from a test strip or the like The housing 14 of the insert 1 has an exterior 17 and interior 16 and contains an opening, such as a receiving port 2, for insertion of test strips 11. A series of discrete electrical light sources, for example a plurality of light emitting diodes (LEDs), can be mounted on a printed circuit board, for example on the top surface of the printed circuit board, located within a housing. The LEDs can be configured and current driven to emit an illumination pattern suitable for reflecting from the test strip, for example, located directly above the LEDs. Light from the LEDs can be reflected off the test strip and through an aperture in the circuit board. The light reflected through the circuit board can be directed to a first mirror mounted under the circuit board. The first mirror can direct the light through a focusing lens to a second mirror. The second mirror can direct the focused light onto an optical detector mounted beneath the circuit board. The optical detector can output a data stream that can be converted by an on onboard central processing unit into a series of 128 distinct one-dimensional numeric readings. The 128 readings can be taken multiple separate times and averaged.

In an alternative embodiment of the disclosure, the positioning of the sensor and the light source can be inverted. For example, in such an embodiment of an optical system, the circuit board may be mounted upside down and, thus, the test strip 11 is located below the circuit board and LEDs. In this embodiment, the LEDs would, therefore, illuminate the strip 11 from above. Therefore, it is in the spirit of the invention for the insert to protect the sensor from contaminants associated with the test strip 11, regardless of the orientation of the sensor and light source within the reader.

In another embodiment, in which a charged coupled device (CCD) or complementary metal oxide semiconductor (CMOS) image sensor, the reader can be programmed to analyze the test strip through two-dimensional readings, rather than through the one dimensional, 1×128, readings. For example, a 5×128,r 512×492, or any of a variety of matrices of "pixels." Such a 2-dimensional reading widens the reflectance capture area to capture reflectance directly from the sides of the test strip.

The optical system may include a plurality of LEDs or, alternatively, one LED is used with an optional feedback loop. The feedback loop can use a photodiode to sense light output variation from the single LED. If light output changes a signal is sent so that an appropriate adjustment can be made, for example, an increase or decrease in current to the LED. Light output from the LED may be reflected either directly off the test strip or, alternatively, directed to a first mirror for reflection to, and then off of the test strip to a second mirror. The second mirror directs the light through a lens to an imager, for example a CCD or CMOS imager.

Figure 12:
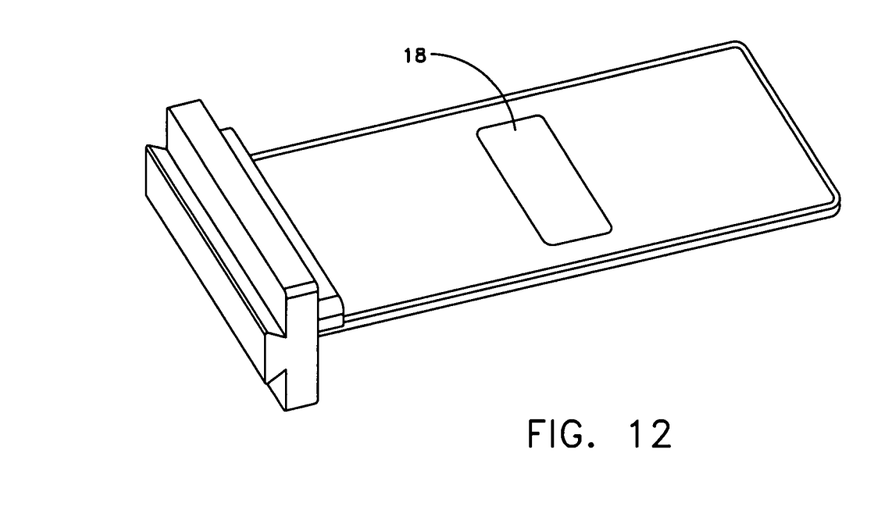
FIG. 12 is a perspective view of an embodiment of a barrier in which only part of the barrier is optically clear.

Regardless of the type of sensor used, or the source of the light within the light path of an optical system, there can be an optically clear removable barrier 3. The removable barrier 3 can block dust/debris, created by the statistic buildup caused by touching and rubbing of elements in the housing 14, from the test strip 11 from contaminating the sensor itself or other system parts used with the sensor such as lenses and mirrors. The barrier 3 can be removable and cleanable or can be removable and disposable. The removable barrier 3 can be the only barrier used or be in addition to a fixed window covering other portions of the optics. In one embodiment, the barrier 3 material includes clear polyvinyl chloride (PVC) plastic with antistatic coating. An alternative embodiment may include silica/quartz glass. The barrier 3 can be mounted on a slide and inserted into the reader device 12 between the test strip area and the sensor. In yet a further embodiment of the disclosure, as shown in FIG. 12, the window 18 may cover only a portion of barrier 3. For example, window 18 may be a center portion of barrier 3 aligned between the test strip 11 and the sensor. Again, in this embodiment, the partial window 18 of the removable barrier 3 may be constructed of a clear, optical material.

Regardless of the presence of the optically clear barrier 3, it is possible that dust and debris will infiltrate into the reader sensor, or system parts used with the sensor, for example the optical sensor mechanism. Therefore, an air inlet 4 can be provided within the insert 1 to allow air, such as compressed air, to be funneled into the housing interior 16 to remove dust, debris, and the like for improved accuracy of the reader 12. The air inlet 4 can be covered with a removable cap 5. In use generally, the removable barrier 3 is removed, and the cap 5 is removed. Air is then blown through the reader 12, as for example through the interior housing 16, so that debris collected on or near the reader sensor is removed. To avoid unwanted dust and debris when the air inlet 4 is not in use, the removable cap 5 can be used to cover air inlet 4. Tether 15 can further affix the removable cap 5 to the air inlet 4. A secondary debris cap can also be configured to shield and protect the light source and censor from dust and debris. The debris cap can be a fixed to the housing 14 or removable, such as a hard cap, tape, or the like.

Figure 1:
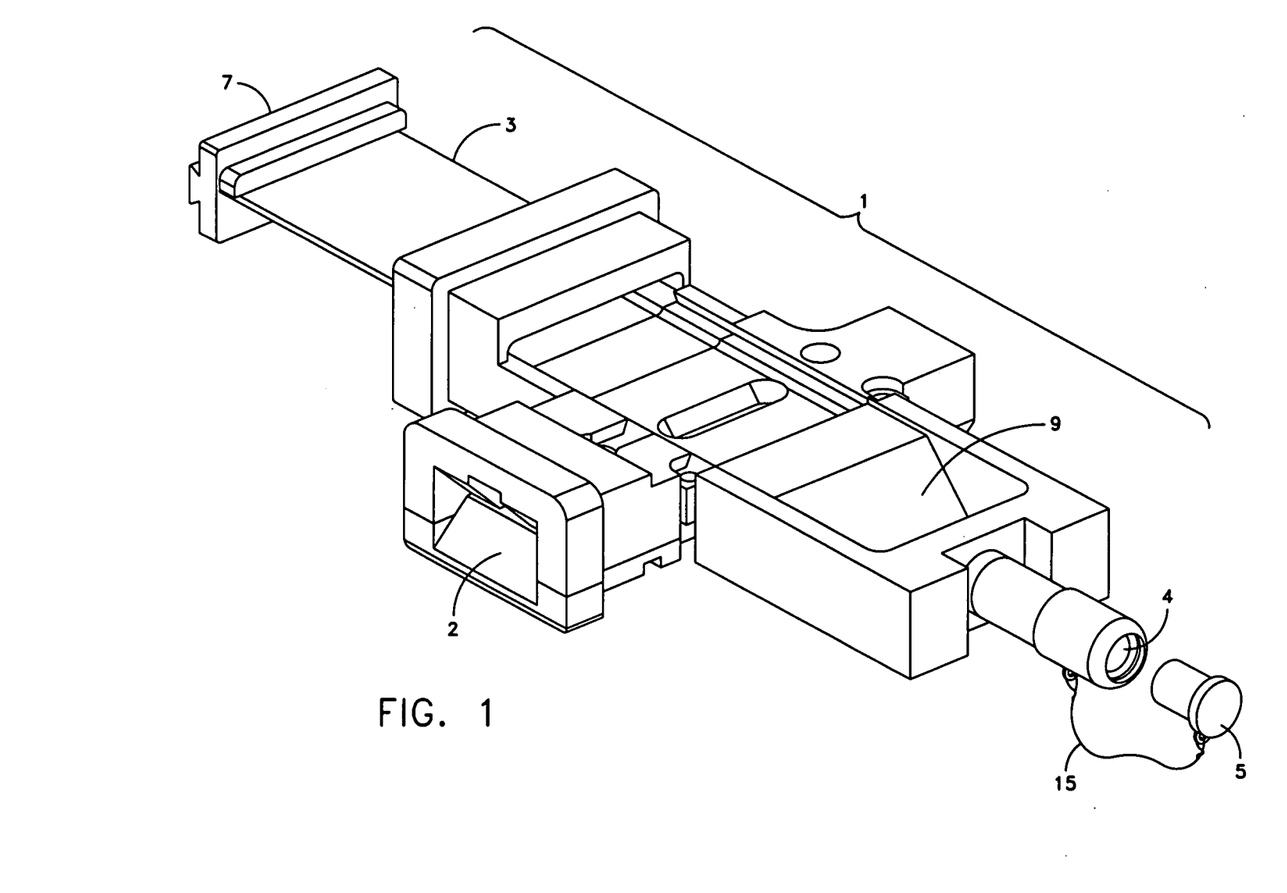
FIG. 1 is a partial perspective showing a module of the insert, where the barrier is partially withdrawn from the insert and the air inlet cap is removed.
Figure 2:
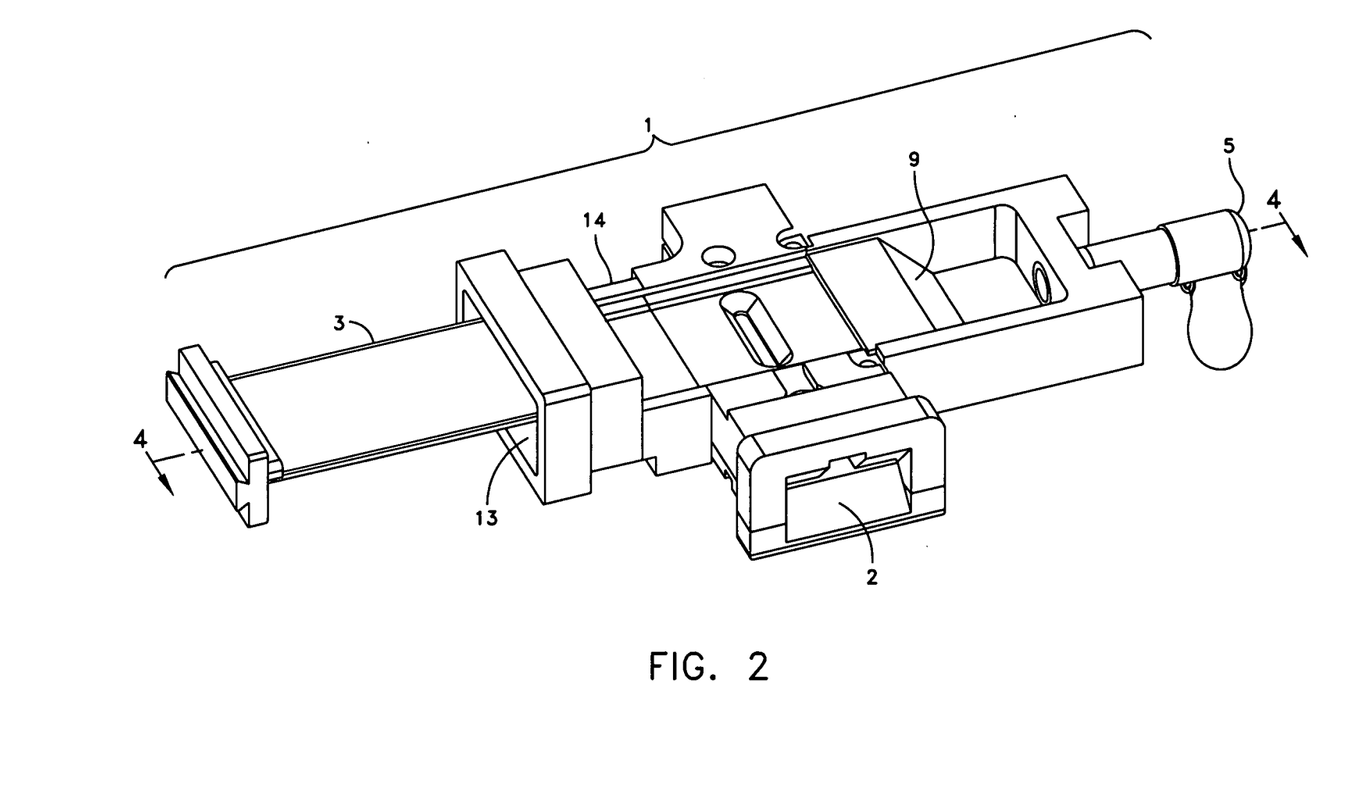
FIG. 2 is a partial perspective showing a module of the insert, where the barrier is partially withdrawn from the insert and the air inlet cap is affixed to the air inlet.
Figure 3:
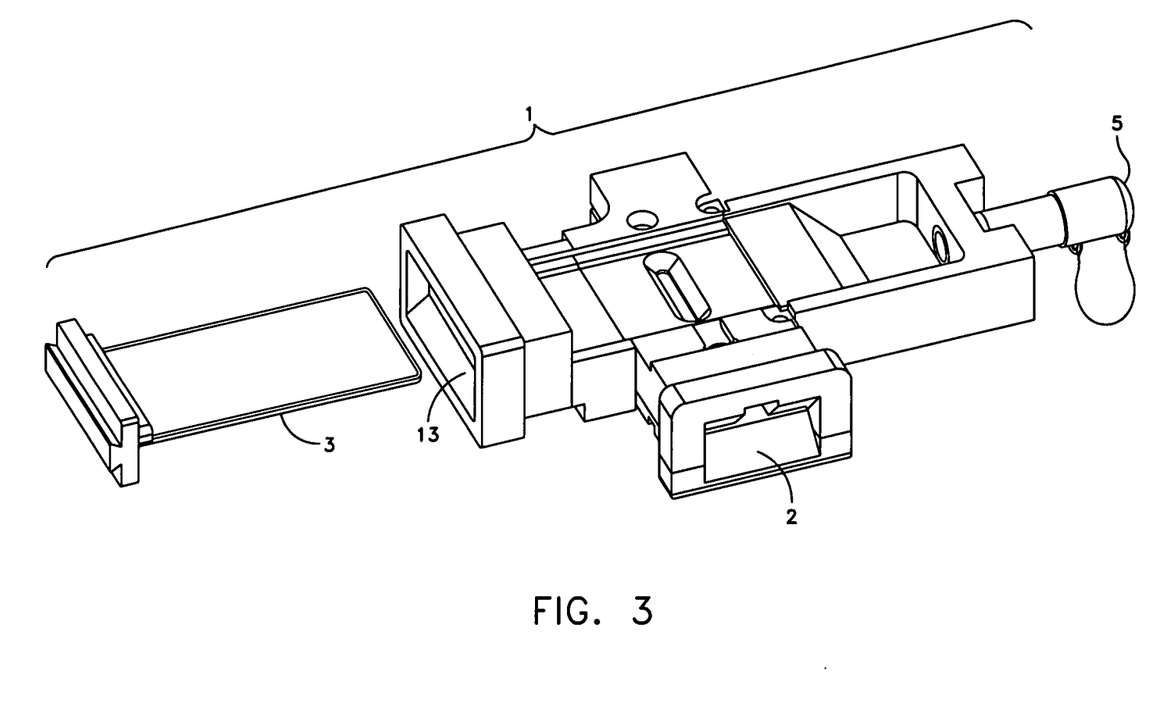
FIG. 3 is a partial perspective showing a module of the insert, where the barrier is withdrawn from the insert.

FIGS. 1-3, show an insert module 1 into which the test strip 11 is inserted and analyzed. These figures illustrate the removable barrier 3 in the withdrawn position, where the barrier 3 is removed from the cavity 13. The barrier 3 can be removed, for example, for cleaning and/or replacement, by pulling or engaging on the handle 7. During testing, the test strip 11 is inserted into the receiving port 2. In an optical reader, for example, a light source may then be used to illuminate the test strip 11 through an aperture in a circuit board. In this embodiment, light may reflect off the test strip 11, which can then be focused onto an optical sensor positioned relative, for example, from above the aperture.

Figure 4:
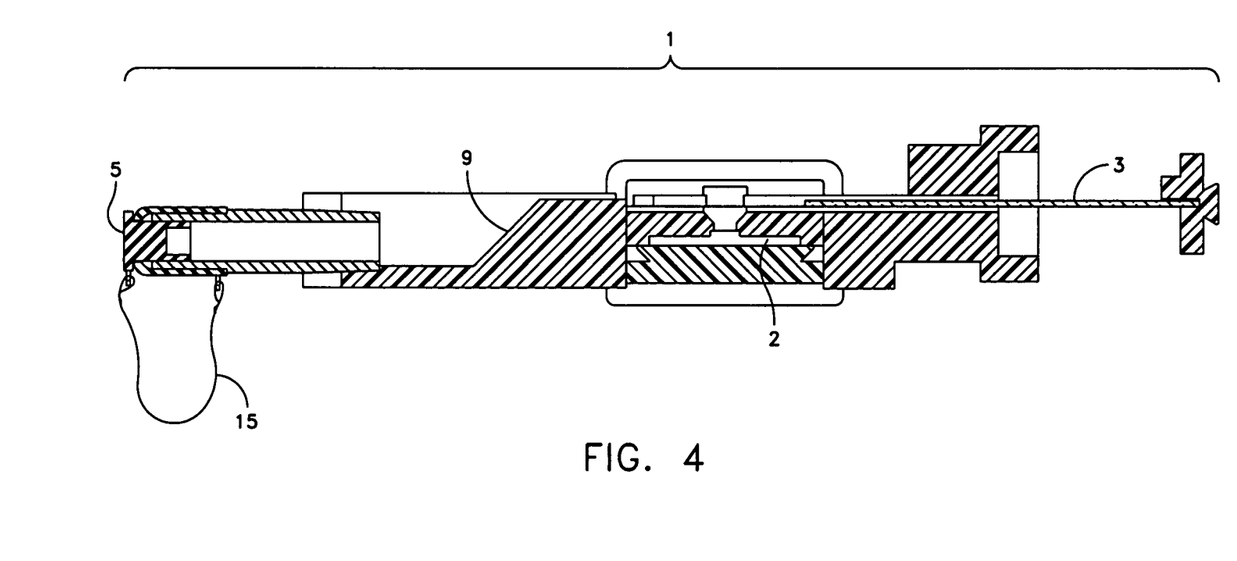
FIG. 4 is a partial cross-section showing a module of the insert, where the barrier is partially withdrawn from the insert.
Figure 5:
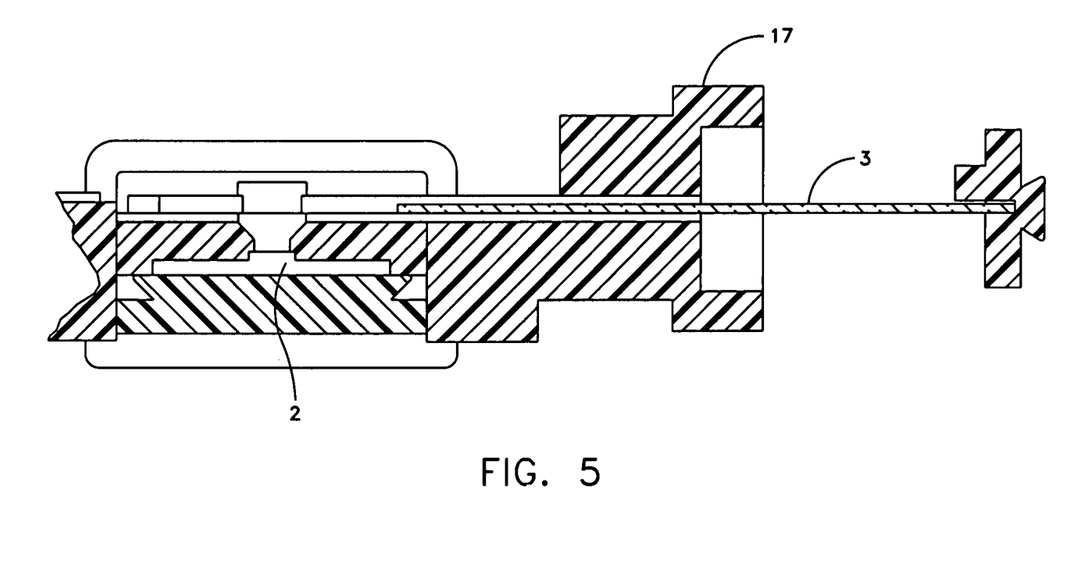
FIG. 5 is an enlarged partial cross-section of a module of the insert, where the barrier is partially withdrawn from the insert.
Figure 6:
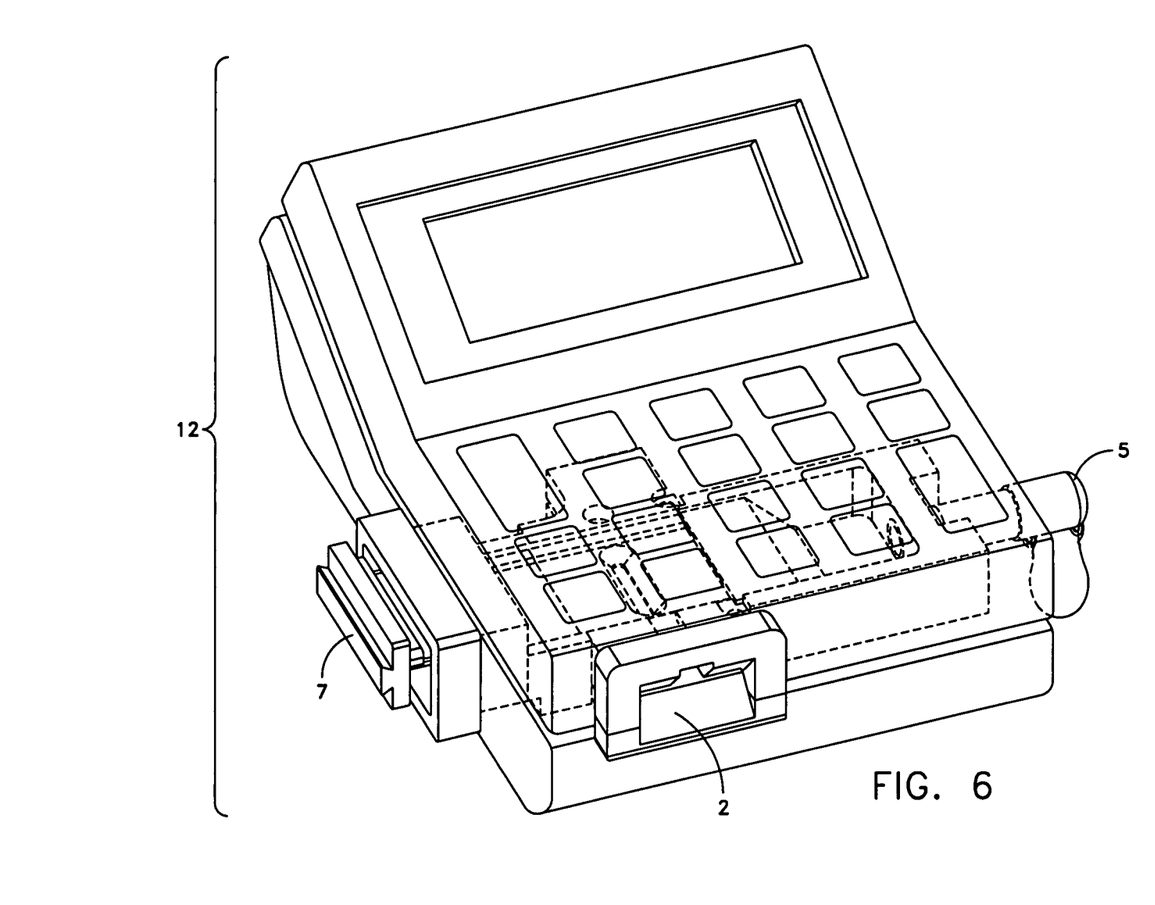
FIG. 6 is an orthographic wire frame view of a module of the insert positioned within the reader.
Figure 7:
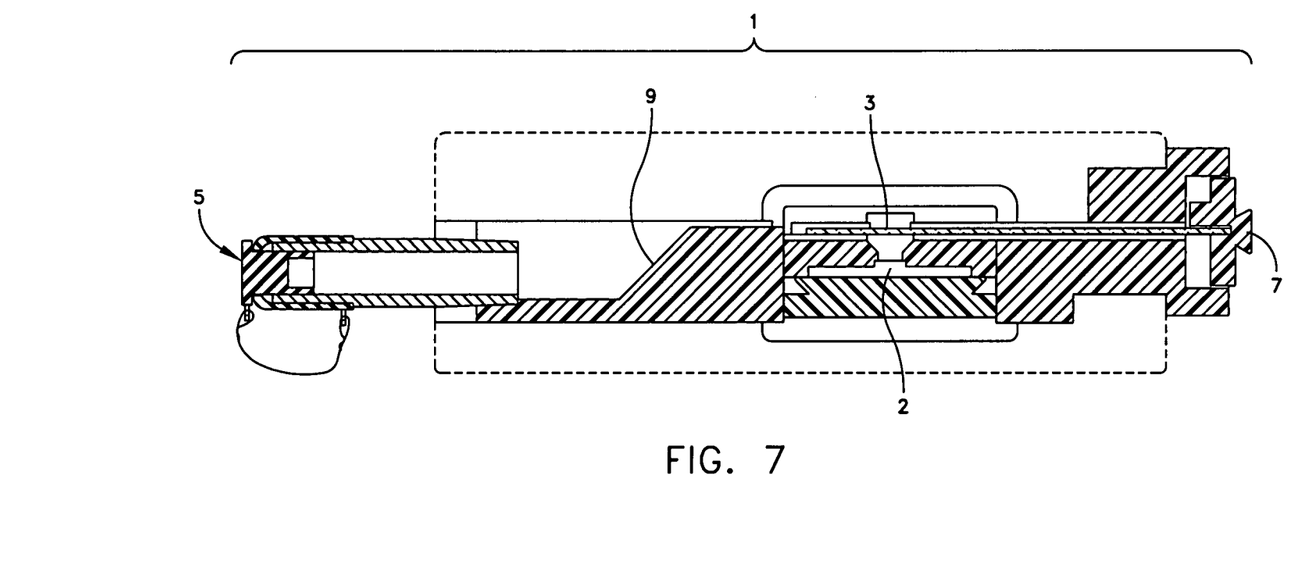
FIG. 7 is a partial cross-section showing a module of the insert, where the barrier is engaged with the insert.

In FIGS. 4 and 5, the removable barrier 3 is withdrawn from the cavity 13, and thus removed from the optics portion of the reader 12. Alternatively, FIGS. 6 and 7 show the removable barrier 3 within the cavity 13, thereby protecting the system's sensors (not shown) which, for example, may reside above the window 3 of the reader 12.

Figure 8:
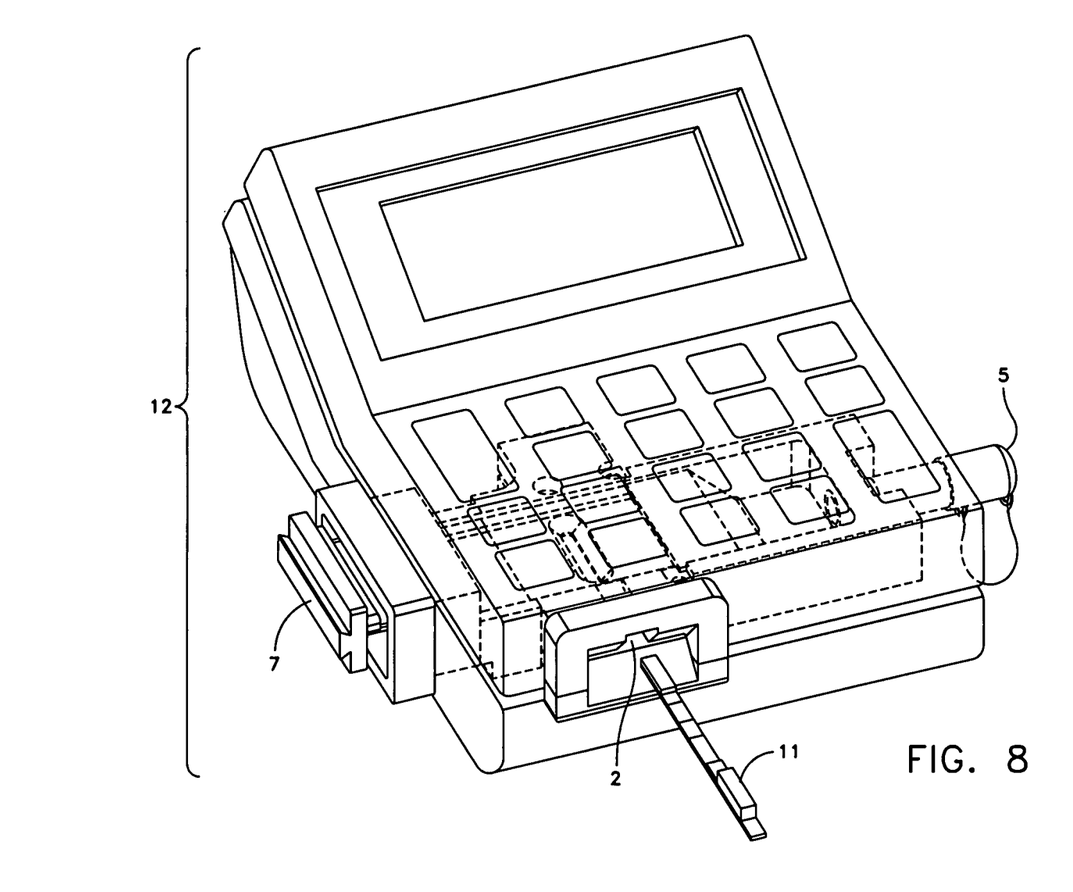
FIG. 8 is an orthographic wire frame view of a module of the insert positioned within the reader and a test strip aligned with the receiving port.
Figure 9:
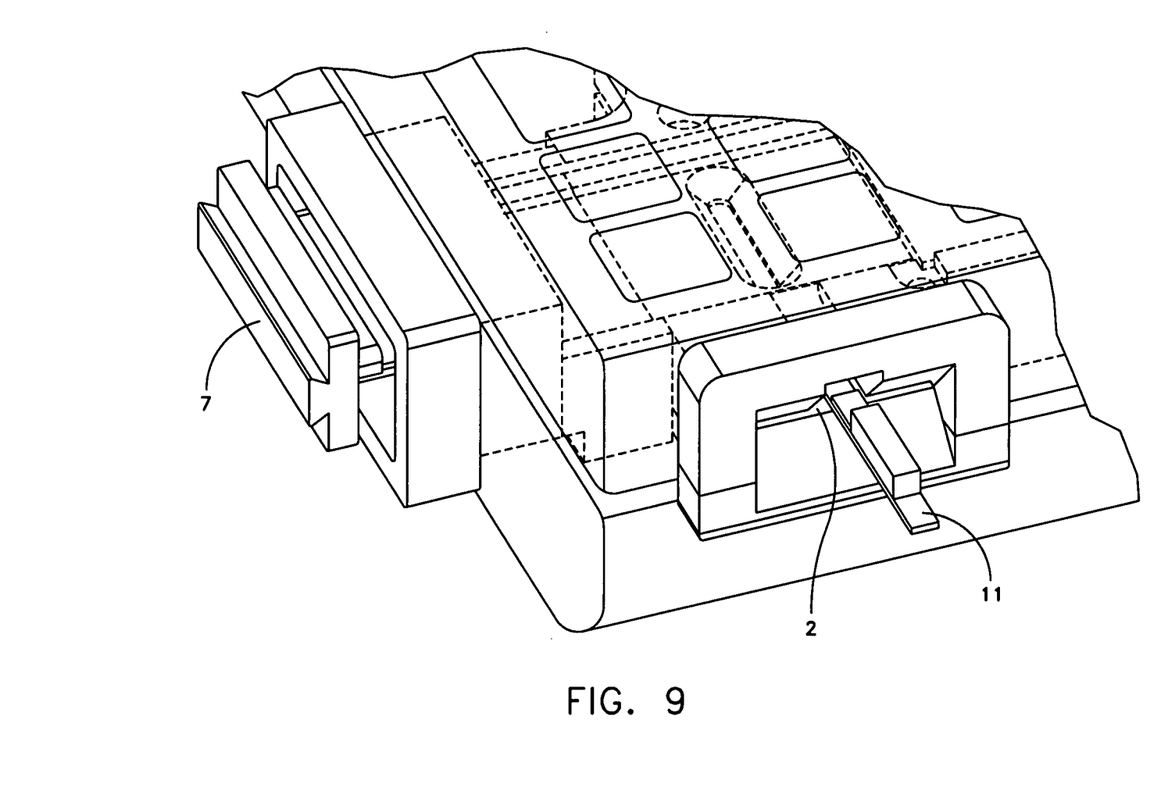
FIG. 9 is an enlarged partial orthographic wire frame view of a module of the insert showing the barrier engaged with the insert and the test strip introduced into the insert.
Figure 10:
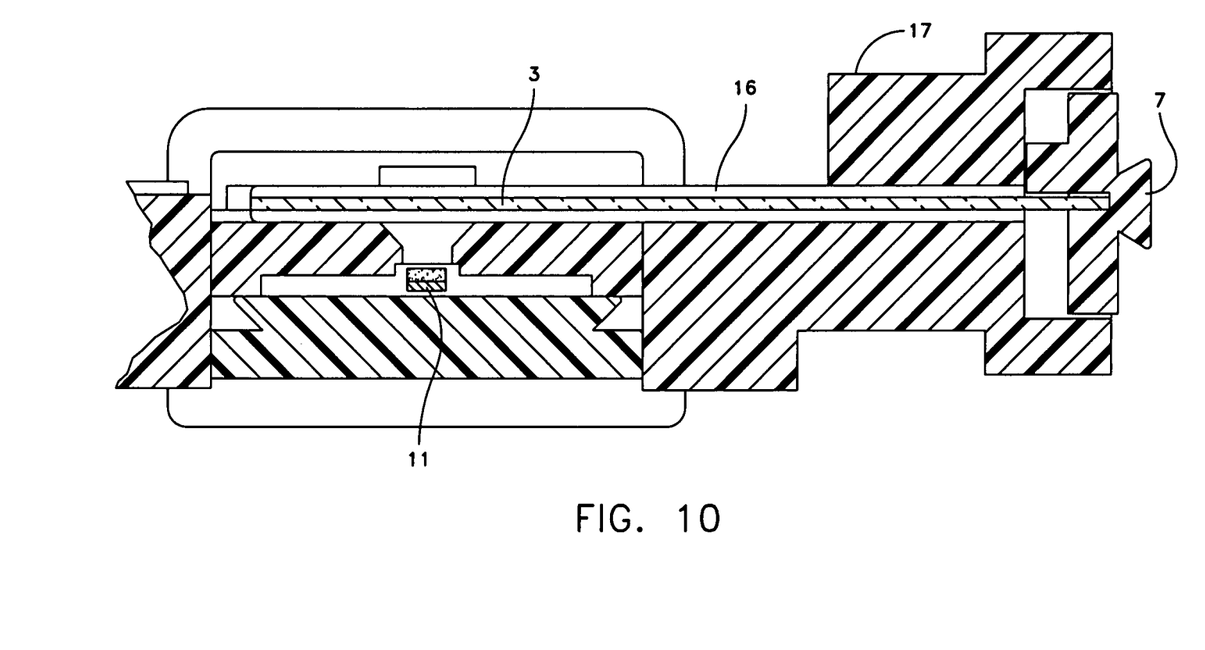
FIG. 10 is an enlarged partial cross section of a module of the insert showing the barrier engaged with the insert and a test strip inserted in the reader.

In FIGS. 8-10, the test strip 11 is inserted into the receiving port 2. When the barrier 3 is in place within cavity 13, the sensors (which can include mirrors and fixed windows but not shown) above the aperture 6 are at least partially, but can be fully, protected from dust, debris, or the like from the strip 11 or elsewhere.

Figure 11:
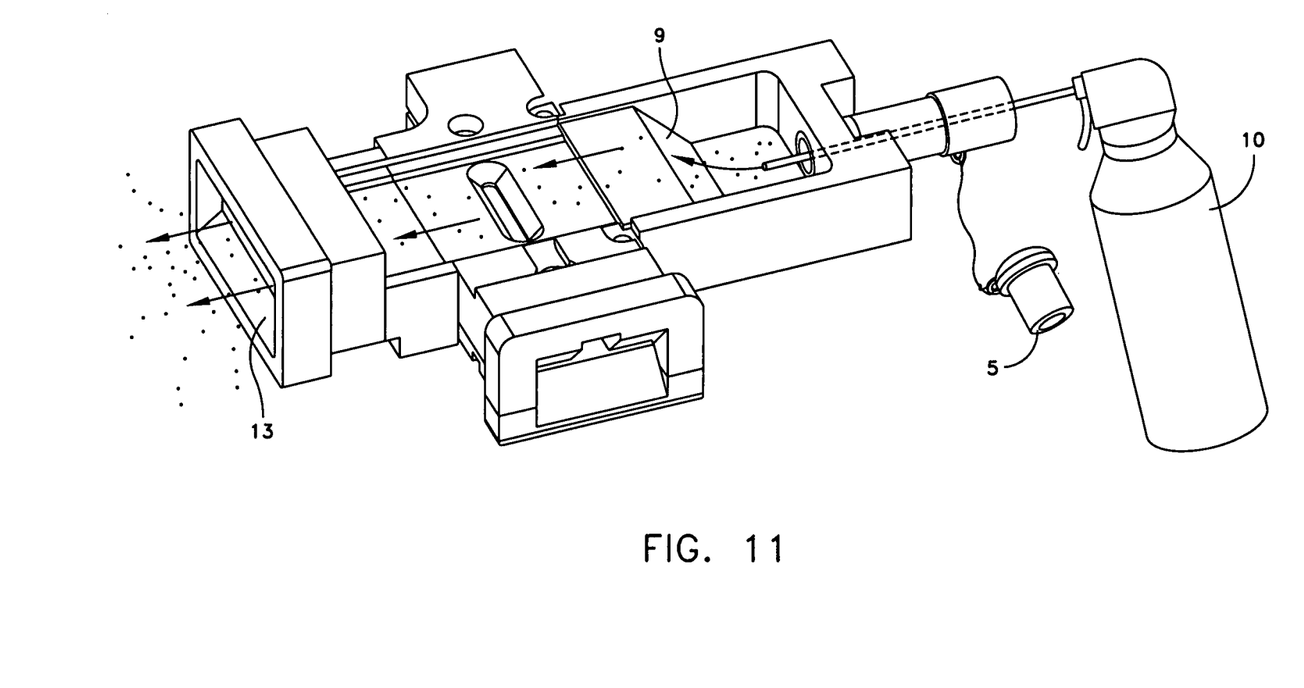
FIG. 11 is a perspective view of a module of the insert, where the barrier and cap are removed and an air source is blowing debris across the insert.

In FIG. 11, an air source 10, such as a compressed air container, can be used to push or blow air through the module 1 of the reader 12. Ridge 9 is provided to reduce, or even block entirely, moisture droplets from the air source 10 from entering the sensor or the lighting portion of the module 1. Air is funneled over the ridge 9 and exits, for example through cavity 13, the insert 1. Dust, debris, and the like that may be in position to disrupt optical sensing or restrict accurate analysis can thereby be removed.

Numerous embodiments and advantages of the insert apparatus and method have been set forth in the foregoing description. Many of the novel features are captured in the following claims. The disclosure, however, is illustrative only, and modifications by one of skill in the art may be made with the present specification and drawings without departing from the scope of the invention.

The invention claimed is:

1. An insert for a lateral flow assay reader, the reader having a light source and an optical detector being configured to align a test strip, positioned within the insert, with a sensor to detect an assay result, the insert comprising:
   a) a housing having an exterior, an interior, and a receiving port, wherein said exterior and said interior define a cavity to receive a removable barrier and has a depth to allow the barrier to align between the test strip and the sensor and wherein the receiving port is adapted to accept the test strip from the exterior of the housing to the interior of the housing; and
   b) a removable optically transparent barrier removably positioned in the cavity,
   whereby the test strip is exposed to the sensor.

2. The device of claim 1, wherein the barrier further comprises an optical window.

3. The device of claim 1, wherein the barrier is positioned on the exterior housing.

4. The device of claim 1, wherein the barrier further comprises a handle to engage and remove the barrier from the insert.

5. The device of claim 1, wherein the barrier is cleanable.

6. The device of claim 1, wherein the barrier comprises clear polyvinyl chloride plastic.

7. The device of claim 1, wherein the barrier comprises glass.

8. The device of claim 1, wherein the barrier comprises a clear optical slide.

9. The device of claim 1, wherein the housing further comprises an aperture positioned relative to the receiving port, whereby the test strip is exposed to the sensor through the aperture.

10. The device of claim 1, further comprising an air inlet within the housing and being configured to allow air to be blown in the device.

11. The device of claim 10, further comprising a ridge positioned between the inlet and the receiving port, whereby the ridge is configured to reduce moisture from entering the interior when air is blown in the device.

12. The device of claim 1, wherein the test strip comprises nitrocellulose.

13. The device of claim 1, wherein the sensor is an optical sensor that detects light refraction on the test strip.

14. The device of claim 13, further comprising a light source aligned with the sensor, wherein the insert if positioned between the light source and the sensor.

15. The device of claim 14, wherein the light source comprises a light emitting diode and wherein the light emitting diode is positioned diode is positioned on a printed circuit board.

16. The device of claim 13, wherein the optical sensor is material selected from the group consisting of: a single photodiode, multiple photodiodes, a linear photodiode array, a charged couple device and a complimentary metal oxide semiconductor image sensor.

17. A lateral flow assay reader having an insert, a light source and an optical detector, the lateral flow assay reader being configured to align a test strip, positioned within the insert, with the optical detector to detect an assay result, the insert comprising:
   a) a housing having an exterior, an interior, and a receiving port
   within the housing, the receiving port being configured to accept the test strip from the exterior of the housing to the interior of the housing; and
   b) a removable optically transparent barrier, having a handle to removably position the optically transparent barrier in the insert,
   wherein the barrier is aligned between the test strip and the detector.

18. The device of claim 17, wherein the barrier further comprises an optical window.

19. The device of claim 17, wherein the barrier is cleanable.

20. The device of claim 17, wherein the exterior housing further comprises an aperture positioned relative to the receiving port, whereby the test strip is exposed to the sensor through the aperture.

21. The device of claim 17, further comprising an air inlet within the housing and being configured to allow air to be blown in the device.

* * * * *